US011886686B2

(12) United States Patent
Gold et al.

(10) Patent No.: US 11,886,686 B2
(45) Date of Patent: Jan. 30, 2024

(54) USER INTERFACE, SYSTEM, AND METHOD FOR OPTIMIZING A PATIENT PROBLEM LIST

(71) Applicant: Intelligent Medical Objects, Inc., Northbrook, IL (US)

(72) Inventors: Jonathan Gold, Louisville, CO (US); Steven Rube, Lake Forest, IL (US); David Arco, Chicago, IL (US); David Chen, Wheeling, IL (US)

(73) Assignee: Intelligent Medical Objects, Inc., Rosemont, IL (US)

( * ) Notice: Subject to any disclaimer, the term of this patent is extended or adjusted under 35 U.S.C. 154(b) by 0 days.

(21) Appl. No.: 16/115,271

(22) Filed: Aug. 28, 2018

(65) Prior Publication Data

US 2020/0073516 A1    Mar. 5, 2020

(51) Int. Cl.
| | |
|---|---|
| *G06F 3/0482* | (2013.01) |
| *G16H 10/60* | (2018.01) |
| *G06F 3/0483* | (2013.01) |
| *G06F 40/284* | (2020.01) |

(52) U.S. Cl.
CPC .......... *G06F 3/0482* (2013.01); *G06F 3/0483* (2013.01); *G06F 40/284* (2020.01); *G16H 10/60* (2018.01)

(58) Field of Classification Search
CPC ............. G06F 16/9562; G06F 3/0482; H04M 1/27455; G16H 10/60
See application file for complete search history.

(56) References Cited

U.S. PATENT DOCUMENTS

| | | | |
|---|---|---|---|
| 8,589,400 B2 | 11/2013 | Naeymi-Rad | |
| 8,612,448 B2 | 12/2013 | Naeymi-Rad | |
| 8,751,501 B2 | 6/2014 | Naeymi-Rad | |
| 2014/0122117 A1 | 5/2014 | Masarie, Jr. | |
| 2015/0154362 A1* | 6/2015 | Masarie, Jr. | G16H 70/20 705/3 |
| 2015/0242571 A1 | 8/2015 | Naeymi-Rad | |
| 2016/0139736 A1* | 5/2016 | Frank | G06Q 10/02 705/5 |
| 2016/0182613 A1* | 6/2016 | Brune | G06F 1/1698 709/217 |
| 2017/0083669 A1* | 3/2017 | Surprenant | G16H 10/60 |
| 2017/0116373 A1* | 4/2017 | Ginsburg | G16H 10/40 |
| 2017/0213001 A1* | 7/2017 | Harrison | G16H 40/63 |
| 2018/0174684 A1* | 6/2018 | Eastman | G06N 20/00 |
| 2018/0357381 A1* | 12/2018 | Aldin | G06F 40/197 |
| 2021/0005318 A1* | 1/2021 | Eastman | G16H 80/00 |

* cited by examiner

*Primary Examiner* — Beau D Spratt
*Assistant Examiner* — Amy P Hoang
(74) *Attorney, Agent, or Firm* — Quarles & Brady LLP (57) ABSTRACT

A user interface, system and method for optimizing a patient problem list in an electronic medical record or electronic health record in which entries in the problem list are removable or otherwise editable if they were entered into the problem list longer ago than a limited duration window to which the entries are categorized. In order to determine that categorization, the problem list entries are mapped to concepts or lexicals of an interface terminology, which in turn is mapped to concepts of another terminology, and those concepts are analyzed with respect to one or more criteria used to establish the limited duration window.

14 Claims, 11 Drawing Sheets

IMO
Intelligent Medical Objects

Select 'Hourglass On'
Northbrook IMO Hospital

Patient: Mary,.....
Pt ID: 002xxxxxx
Registries: Diabetes, Heart Failure, Hypertension Age: 85    Gender: Female
Date of Birth: 0x/xx/19xx Intelligent Problem List

[A-Z] [HCC Off] [Hourglass On]    [Display Duplicates]    View ▼    New

Acute right heart failure (HCC)    9/29/2017
Cardiogenic shock (HCC)    9/29/2017
Heart failure, acute on chronic, systolic and diastolic (HCC)    9/29/2017
Ischemic cardiomyopathy    10/22/2017
Paroxysmal atrial fibrillation (HCC)    9/29/2017
Triple vessel coronary artery disease    9/29/2017
Ventricular tachyarrhythmia (HCC)    11/29/2017

Abnormal LFTs (liver function tests)    9/29/2017
Right upper quadrant abdominal pain    9/29/2017

Acute on chronic renal insufficiency    9/29/2017
Bacterial vaginosis    9/29/2017
CKD (chronic kidney disease) stage 3, GFR 30-59 ml/min    10/20/2017
E. coli UTI    9/29/2017
Vaginitis and vulvovaginitis    9/29/2017

Colonization with VRE (vancomycin-resistant enterococcus)    9/29/2017

Anxiety disorder due to medical condition    9/29/2017
History of depression    9/29/2017

Acute respiratory failure following trauma and surgery (HCC)    10/23/2017
Chronic obstructive pulmonary disease (COPD) (HCC)    11/29/2017

Bilateral edema of lower extremity    9/29/2017
Postoperative fever    9/29/2017

▲ Import
▲ IMO Tools and Reference Links

FIG. 5

IMO®
Intelligent Medical Objects

Double-click on "Acute right heart failure (HCC)"
Northbrook IMO Hospital

Patient: Mary.....  Age: 85  Gender: Female
Pt ID: 002xxxxxx  Date of Birth: 0x/xx/19xx
Registries: Diabetes, Heart Failure, Hypertension

| A-Z | HCC Off | Hourglass Off | Intelligent Problem List | Display Duplicates | View ▼ | New |

Cardiovascular
Acute right heart failure (HCC) 9/29/2017
Cardiogenic shock (HCC) 9/29/2017
Heart failure, acute on chronic, systolic and diastolic (HCC) 9/29/2017
Ischemic cardiomyopathy 10/22/2017
Paroxysmal atrial fibrillation (HCC) 9/29/2017
Triple vessel coronary artery disease 9/29/2017
Ventricular tachyarrhythmia (HCC) 11/29/2017

Genitourinary and Abdominal
Abnormal LFTs (liver function tests) 9/29/2017
Right upper quadrant abdominal pain 9/29/2017

Genitourinary and Reproductive
Acute on chronic renal insufficiency 9/29/2017
Bacterial vaginosis 9/29/2017
CKD (chronic kidney disease) stage 3, GFR 30-59 ml/min 10/20/2017
E coli UTI 9/29/2017
Vaginitis and vulvovaginitis 9/29/2017

Infectious Diseases
Colonization with VRE (vancomycin-resistant enterococcus) 9/29/2017

Neuropsych
Anxiety disorder due to medical condition 9/29/2017
History of depression 9/29/2017

Pulmonary
Acute respiratory failure following trauma and surgery (HCC) 10/23/2017
Chronic obstructive pulmonary disease (COPD) (HCC) 11/29/2017

Symptoms and Signs
Bilateral edema of lower extremity 9/29/2017
Postoperative fever 9/29/2017

▲ Import
▲ IMO Tools and Reference Links

Select "Colonization with VRE (vancomycin-resistant enteroccocus)"

Northbrook IMO Hospital

IMO
Intelligent Medical Objects

Patient: Mary.....  Age: 85  Gender: Female
Pt ID: 002xxxxxx  Date of Birth: 0x/xx/19xx
Registries: Diabetes, Heart Failure, Hypertension

[A-Z]  [HCC Off]  [Hourglass Off]   Intelligent Problem List   [Display Duplicates]   View ▼   New Cardiogenic shock (HCC)  9/29/2017
Heart failure, acute on chronic, systolic and diastolic (HCC)  9/29/2017
Ischemic cardiomyopathy  10/22/2017
Paroxysmal atrial fibrillation (HCC)  9/29/2017
Triple vessel coronary artery disease  9/29/2017
Ventricular tachyarrhythmia (HCC)  11/29/2017

Abnormal LFTs (liver function tests)  9/29/2017
Right upper quadrant abdominal pain  9/29/2017

Acute on chronic renal insufficiency  9/29/2017
Bacterial vaginosis  9/29/2017
CKD (chronic kidney disease) stage 3, GFR 30-59 ml/min  10/20/2017
E. coli UTI  9/29/2017
Vaginitis and vulvovaginitis  9/29/2017

Colonization with VRE (vancomycin-resistant enteroccocus)  9/29/2017

Anxiety disorder due to medical condition  9/29/2017
History of depression  9/29/2017

Acute respiratory failure following trauma and surgery (HCC)  10/23/2017
Chronic obstructive pulmonary disease (COPD) (HCC)  11/29/2017

Bilateral edema of lower extremity  9/29/2017
Postoperative fever  9/29/2017

▲ Import
▲ IMO Tools and Reference Links

USER INTERFACE, SYSTEM, AND METHOD FOR OPTIMIZING A PATIENT PROBLEM LIST

BACKGROUND

1. Field of the Invention

The present application is directed to a user interface, a system, and a method for optimizing a patient problem list that is generated in conjunction with electronic medical record ("EMR") or electronic health record ("EHR") software.

2. Description of the Related Art

Patient problem lists are an integral part of EMR and EHR software, providing clinicians with a way to evaluate a patient's medical history. At each care event, a clinician may assess a patient's current condition to determine the status of pre-existing conditions and/or to determine whether the patient is presenting with any new problems. Those problems may be entered into the patient's problem list in order to provide an accurate representation of the patient's history.

In some instances, those problem list entries are normalized to provide consistency from one list to the next. For example, one patient's problem list may indicate "heart attack," another's may indicate "myocardial infarction," and a third may indicate simply "m.i." Certain EMR and EHR software programs may normalize these entries so that they all indicate "myocardial infarction." Ideally, however, entries in a problem list are maintained in the same or a substantially identical form as the manner in which they originally were entered. While keeping those entries in their original form preserves the contextual, semantic meanings attached to the problems that the clinician or other data inputter intended, the lack of standardized data also can make post-processing or other analysis of bulk EMR or EHR records exceedingly difficult.

Additionally, as problems are revised and new problems are added in subsequent visits, a presentation of the user's problem history may grow and become increasingly more difficult to decipher quickly. In one instance, the EMR or EHR software may arrange the problem list entries in chronological order. While this may provide a clinician with a way to evaluate relative ages of the problem list entries, it may not provide the clinician with sufficient information to evaluate the present significance of those entries.

Still further, there are a plurality of different EMR or EHR software programs, including software provided by companies like Allscripts, Cerner, NextGen, etc. Each of those programs structures and presents data in unique ways, which can make it difficult to implement changes that affect those different programs without the need for significant customization, increasing the time and cost needed to do so.

What are needed are a system and method that preferably address one or more of these challenges.

BRIEF SUMMARY

In one aspect, a dynamically-adjustable user interface for modifying a patient problem list in an electronic medical record or an electronic health record includes a first region comprising a plurality of patient problem list entries. Each problem list entry is encoded with a date of entry into the patient problem list and at least one concept or lexical of an interface terminology. The at least one concept or lexical is mapped to at least one external terminology concept. One or more of the at least one external terminology concepts is mapped to a limited duration group, the limited duration group including a limited duration window. The date of entry of each problem list entry is compared against the limited duration window. When the date of entry of a problem list entry from among the plurality of patient problem list entries is outside the limited duration window, the first region is modifiable to remove the problem list entry from the first region In another aspect, a method for dynamically-adjusting a patient problem list in an electronic medical record or an electronic health record includes the steps of displaying a plurality of patient problem list entries, encoding each problem list entry with a date of entry into the patient problem list and at least one concept or lexical of an interface terminology, mapping the at least one concept or lexical to at least one external terminology concept, mapping the at least one external terminology concept a limited duration group that includes a limited duration window, and comparing the date of entry of each problem list entry against the limited duration window. When the date of entry of a problem list entry from among the plurality of patient problem list entries is outside the limited duration window, the patient problem list is modifiable to remove the problem list entry from the patient problem list.

BRIEF DESCRIPTION OF THE SEVERAL VIEWS OF THE DRAWINGS

FIG. 5 is a screenshot of the problem list of FIG. 4 after analyzing the problem list entries with respect to one or more limited duration groups;

FIG. 8 is a screenshot of the problem list of FIG. 5 after being updated to reflect the user's selection indicated in FIG. 7;

DETAILED DESCRIPTION

As discussed in greater detail below and with reference to the accompanying figures, the present user interface, system, and method provide for dynamically identifying specific problems of interest in the problem list of an electronic medical record or an electronic health record for reconsideration, thereby reducing the effort needed by the clinician to review the problem list and increasing the efficiency by which the problem list presents relevant information and by which the clinician is able to interface with the software.

Affected problem list entries include those that have a finite duration. The length of time that makes a problem "finite" may depend on the specific problem. For example, the system may treat a problem as "finite" if a clinician would expect it to be resolved within a few days, a few weeks, or a few months.

Figure 1:
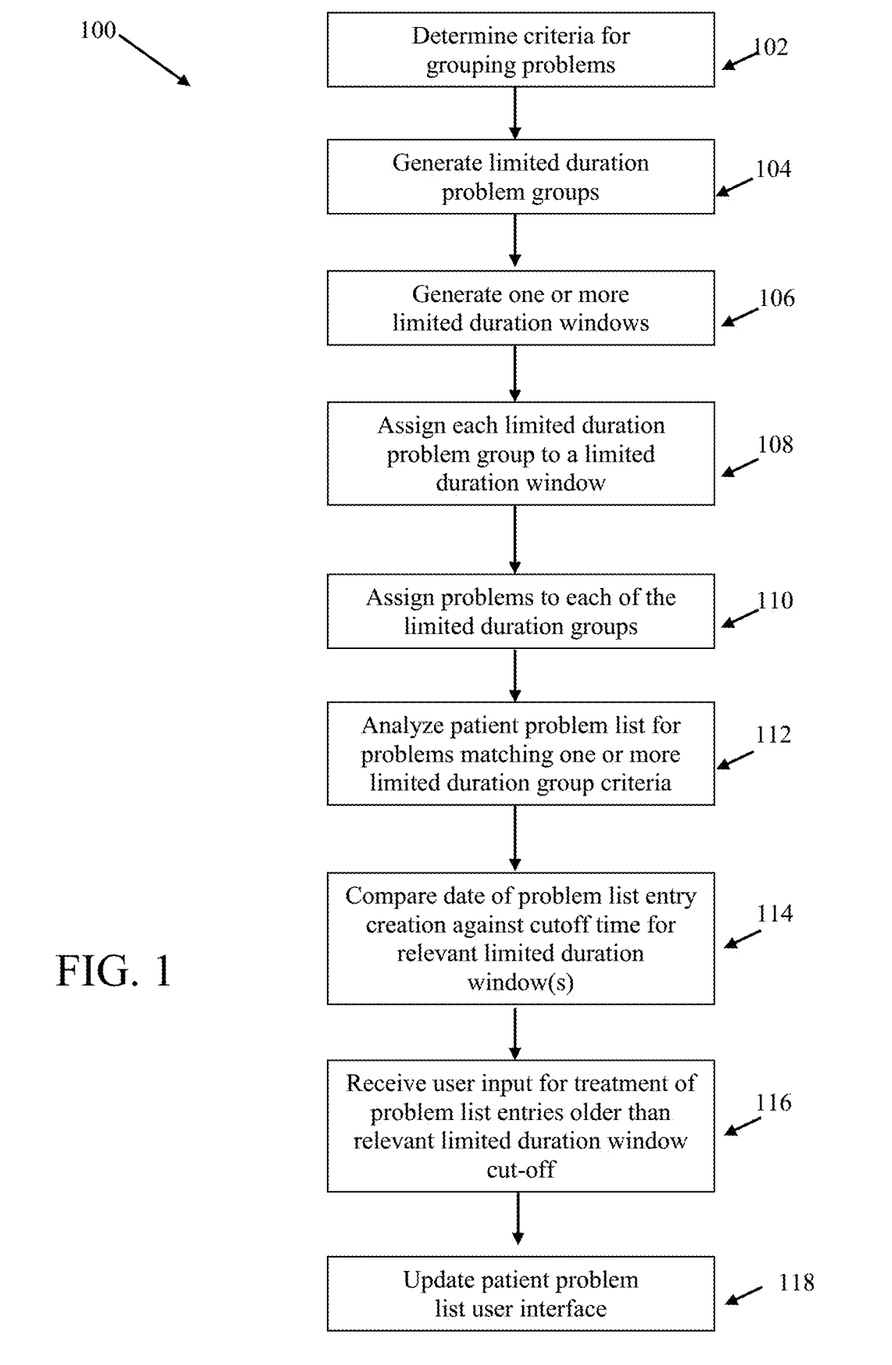
FIG. 1 is a flowchart depicting one exemplary method of optimizing a patient problem list in an EMR or EHR.

Turning to FIG. 1, the system employs a series of heuristics to accomplish duration modeling of a plurality of problems within a problem list. First, with regard to method 100 and at step 102, the system may determine a plurality of criteria by which problems may be evaluated and/or grouped. Factors to be considered may include, e.g.: 1) whether the problem is one that typically has an acute, short duration such as acute inflammations or acute exacerbations of chronic conditions (i.e., acute-on-chronic problems), 2) whether the condition is self-limited and typically resolves itself without treatment of the underlying etiology, 3) whether the problem is a primary, abrupt insult (injury), 4) whether the problem is one that leads to death if not resolved rapidly, 5) whether the problem is used to document an administrative or health encounter, e.g., a well-baby exam or yearly physical, etc.

Based on these factors, at step 104, the system may generate a plurality of limited duration problem groups, such as: 1) acute diseases, 2) burns, 3) cardiac arrest, 4) cellulitis, 5) cramps, 6) fractures of bone, 7) infectious diseases, 8) inflammation of specific body structures or tissues, 9) necrosis of anatomical sites, 10) physical examinations, 11) postoperative complications, 12) pregnancy, childbirth, and puerperium-related problems, 13) respiratory failures, etc. It will be appreciated that the preceding groups are not intended to be limiting and that more or fewer other limited duration groups may be created.

Next, at step 106, the system may generate one or more duration windows into which problem list entries may be categorized. The windows may be multiples of a predetermined amount, e.g., multiples of 30 day increments. In one aspect, the system may only generate a limited number of windows in order to focus on problems of a limited duration. For example, the system may generate one window, two windows, three windows, four windows, five windows, six windows, seven windows, eight windows, nine windows, ten windows, eleven windows, or twelve windows, where the windows are temporally contiguous with one another.

Once the system has generated the one or more limited duration windows, it may assign each of the groups to a limited duration window, as at step 108. For example, the "acute disease" group may be assigned to a ninety-day window, as may the "cardiac arrest," "cellulitis," "cramps," "infectious disease," "physical examination," and "respiratory failure" groups. Conversely, the "fracture of bone," "inflammation of bone," "necrosis anatomical site," and "postoperative complication" groups may be assigned to the one hundred twenty-day window. "Burns" may be assigned to a one hundred eighty-day window, and the "pregnancy, childbirth, and puerperium" group may be assigned to a two hundred seventy-day window.

In another instance, the system may combine steps 106 and 108 by simply assigning a specific period of time, e.g., a specific number of days, to one or more of the limited duration groups.

Categorization or duration assignation may be based on a subjective determination by one or more individuals. In the event that multiple individuals are consulted to determine duration length for a problem, the system may require consensus in the form of complete agreement, majority agreement, or supermajority (e.g., at least ⅔ or ¾) agreement. Agreement in this context may reflect a determination that 100% of instances of that problem should be resolved within the selected duration. Alternatively, agreement in this context may reflect a determination that fewer than 100% (e.g., about 99%, or about 95%, or about 90%) of instances of the problem should be resolved within the selected duration.

Once the system creates limited duration groups and assigns specific limited time values to each of those groups, the system at step 110 then may assign specific problems to each of the limited duration groups. In the context of electronic health records, these patient problems may be encoded using multiple different ontologies, which may serve different functions in the patient care process. Various ontologies have been developed for various reasons, including administrative code sets that may be designed to support administrative functions of healthcare, such as reimbursement and other secondary data aggregation; clinical code sets that encode specific clinical entities involved in clinical work flow and allow for meaningful electronic exchange and aggregation of clinical data for better patient care; and reference terminology code sets that may be considered a "concept-based, controlled medical terminology" to maintain a common reference point in the healthcare industry. Reference terminologies also identify relationships between their concepts, e.g., relationships can be hierarchically defined, such as a parent/child relationship. Common examples of administrative code sets are the International Classification of Disease (ICD) and the Current Procedural Terminology, which is referred to via the trademark CPT. Examples of clinical code sets are the Logical Observation Identifiers Names and Codes, referred to under the trademark LOINC, and a normalized terminology for medication information, such as the terminology of the National Library of Medicine referred to under the trademark RxNorm. One example of a reference terminology is The Systematized Nomenclature of Medicine—Clinical Terms, referred to under the trademark "SNOMED CT."

In another instance, each problem also may be mapped to another ontology in the form of an interface terminology that recognizes semantic meaning, mapping that interface terminology to the various other ontologies, and then relying on that interface terminology to analyze the practitioner's entries. One example of a system and method for using an interface terminology and the relevant ontology mappings may be found in the commonly-owned U.S. patent publication 2014/0122117, published May 1, 2014, the contents of which are incorporated by reference in their entirety. In that example, the interface terminology comprises a plurality of concepts within one or more domains, and one or more descriptions (lexicals) linked to each concept, where each description reflects an alternative way to express the concept. The interface terminology lexicals then may be mapped to one or more problems represented by one or more of the other ontologies. As one result of this mapping, the system may be able to interface with one or more additional software applications that use different administrative, clinical, and/or reference terminology elements as data inputs while still maintaining the underlying semantic meaning of the data as originally captured by a clinician.

Each concept in the interface terminology may be stored as an entry in a table in a database. The database also may include an attributes table for storing metadata related to each of the concepts. The system may generate a new column in the table for the attribute "DurationDays" and may populate that column with the durations corresponding to each of the duration windows. For example, in the example where the system generates twelve duration windows of equal thirty day lengths, the system may populate the rows of the DurationDays column with the values 30, 60, 90, 120, 150, 180, 210, 240, 270, 300, 330, and 360. The system then may map a pointer between each concept and the relevant DurationDays attribute row in order to ascribe the relevant DurationDays attribute to its respective concept.

In order to determine what the DurationDays attribute value for each interface terminology concept should be, the system may rely on a multiplicity of mappings. First, the system may rely on the mappings between each interface terminology concept and its respective interface terminology lexicals. Second, the system may rely on the mappings between the lexicals and elements of a first external terminology. Third, the system may rely on the mappings between the lexicals and elements of a second external terminology.

In one instance, the system may rely on the first and second external terminologies for inclusionary purposes. In another instance, the system may rely on the first external terminology for inclusionary purposes and the second external terminology for exclusionary purposes. In another instance, the system may rely on the second external terminology for inclusionary purposes and the first external terminology for exclusionary purposes. In another instance, the system may rely on the first external terminology for both inclusionary and exclusionary purposes and the second external terminology for inclusionary or exclusionary purposes. In still another instance, the system may rely on the second external terminology for both inclusionary and exclusionary purposes and the first external terminology for inclusionary or exclusionary purposes. In yet another instance, the system may rely on both the first and second external terminologies for both inclusionary and exclusionary purposes.

In one instance, the first and/or second external terminologies may be hierarchically organized. In one instance, the first external terminology is SNOMED, and the second external terminology is ICD-10-CM.

In particular, the system may build the limited duration groups by receiving a user classification of a plurality of concepts in the second external terminology with regard to one or more of the limited duration groups. For example, the concept "acute disease (disorder)" may be classified in the "acute disease" limited duration group. Similarly, the concept "abrasion and/or friction burn of back without infection" may be classified in the "burn" limited duration group. The system may recognize that certain concepts may be classifiable into more than one limited duration group, in which case the system may classify them into all applicable groups.

The first external terminology may include a hierarchical or other arrangement between its concepts, which the system may use in building the limited duration groups. Thus, upon placement of the "acute disease (disorder)" concept from the first external terminology into the "acute disease" limited duration group, the system also may be configured to include all children, offspring, or hierarchically narrower concepts in the first external terminology to be included in the "acute disease" limited duration group. The system may permit a user to specify the degree to which the hierarchical or other arrangement of concepts in the first and second external terminologies are used to build the limited duration groups. For example, the system may permit the user to rely on only the selected concepts through "include" or "exclude" mappings. Alternatively, the system may present the user with "include as derived," "exclude as derived," "include with offspring," and/or "exclude with offspring" map options. The latter two options relate to the specific external terminology code and other codes hierarchically or otherwise related to that code within the selected external terminology. The former two options may be point specific, so to only relate to the specific concepts that are chosen and not to any of their children or otherwise-related concepts.

In one instance, the first external terminology may be used to build a list of problems in a limited duration group, while concepts in the second external terminology may be used to pare down the possible number of problems. For example, in the "acute disease" example discussed above, the system may determine to exclude a second external terminology concept of "personal history of certain other diseases" from that limited duration group. In this instance, the system may recognize that the specific second external terminology codes that are used modify the relevant problem in such a way that the temporal or finite duration concerns discussed herein become less or irrelevant. Other such concepts may be those that include specific qualifiers associated with patient history or qualifiers whose presence affects the actual temporality of a diagnosis.

In one aspect, the system also may be configured to include or exclude one or more other interface terminology concepts based on criteria other than mappings to the first or second external terminologies. For example, the system may exclude chronic diagnoses from the "acute" limited duration group.

Like the first external terminology, the second external terminology also may include a hierarchical or other arrangement between its concepts. Thus, not only may the system exclude a specified concept within that terminology, but it also may exclude all children, offspring, or hierarchically narrower concepts from the second external terminology from the limited duration group, depending on how the user treats that terminology (e.g., by selecting "exclude as derived" instead of "exclude with offspring").

As discussed above, each of the first and second external terminology concepts may be mapped to a concept in an interface terminology. In particular, each of those concepts may be mapped to a lexical of the interface terminology, which in turn is mapped to an interface terminology concept. Additionally, each first and second external terminology concept may map (indirectly) to only a single respective interface terminology concept. Conversely, however, each interface terminology concept may have multiple first and second terminology concepts that map (indirectly) to it.

Once the limited duration groups have been built and the mappings between those groups and the interface terminology concepts have been generated, the system may be applied to a patient's EMR or EHR to match problems on a patient list with one or more limited duration groups, as at step 112. To accomplish that, the system may analyze the patient record and map each problem presented in the patient's problem list with an interface terminology concept. Rather than normalizing the patient problem list by replacing entries with standardized concepts, the mappings permit the patient's record to maintain the clinician's semantic meaning that is attached to each entry. For each limited duration group, the system may evaluate either the interface terminology concepts (or lexicals) or the first and second external terminology concepts mapped to that group against the interface terminology concepts (or lexical s) or, indirectly, the first and second external terminology concepts mapped to the patient's problem list entries. Problem list entries that, directly or indirectly, map to the relevant first external terminology concepts are then cross-checked to see if they also, directly or indirectly, map to any relevant second external terminology concepts.

If a problem list entry maps to a relevant first external terminology concept and a relevant second external terminology concept, the system ignores that problem list entry. Conversely, if a problem list entry maps to a relevant first external terminology concept but not to a relevant second external terminology concept, the system cross-checks the date of entry of that problem list entry against the DurationDays attribute for the relevant limited duration group, as at step 114. In the event that the problem list entry corresponds to a problem in more than limited duration group, the system may only compare the problem's date of entry against the limited duration group with the smallest DurationDays attribute. If the DurationDays attribute value is greater than the number of days that have elapsed since the problem's date of entry, then the system may ignore that problem. If, however, the DurationDays attribute value is less than or equal to the number of days that have elapsed since the problem's date of entry, the system may flag that problem as one that should have been resolved. The user interface may call out flagged problems in a manner that makes them readily identifiable by a user, e.g., by highlighting those problems, changing the color, font, and/or weight of the letters in the problem, and/or by providing an asterisk or other distinguishing mark next to the flagged problems.

In response, the system may generate an interactive window within the user interface to receive a user input as to how to treat the problem, as at step 116. For example, the interactive window may inform the user that the relevant problem list problem has appeared on the problem for an amount of time greater than or equal to the relevant DurationDays attribute value. The window then may prompt the user to provide an input detailing how to treat the problem list entry. In one aspect, the system may prompt the user to resolve the problem, i.e., simply remove it from the patient's problem list. Alternatively, the system may prompt the user to resolve the problem and then to move or add the problem to the past medical history or past surgical history portion of the patient's record. Still further, the user interface and system may prompt the user to keep the problem on the problem list and suppress alerts for another period of time, e.g., 7 days, or 30 days, or 45 days, or 60 days, or 90 days, or an amount of time equal to the relevant DurationDays attribute value. Additionally, the user interface and system may prompt the user to keep the problem on the problem list and to turn off future alerts for that problem.

In another aspect, if the DurationDays attribute value is less than or equal to the number of days that have elapsed since the problem's date of entry, the system may flag it and all other such problems and generate a separate window or frame in the user interface in which the user can batch evaluate the problems, e.g., using the same options described above.

Once the system has received the user's inputs with regard to each problem that is older than the DurationDays attribute of the limited duration group to which it belongs, the system at step 118 may regenerate, refresh, or otherwise update the problem list to reflect the changes being made. In this manner, the problem list may quickly and intuitively present the user with the patient's most recent or otherwise relevant problems. As such, the user interface presents the user/clinician with a more accurate, timelier picture of the patient's problems, thereby permitting the clinician to provide faster, more responsive, and potentially more accurate care to the patient.

Figure 2:
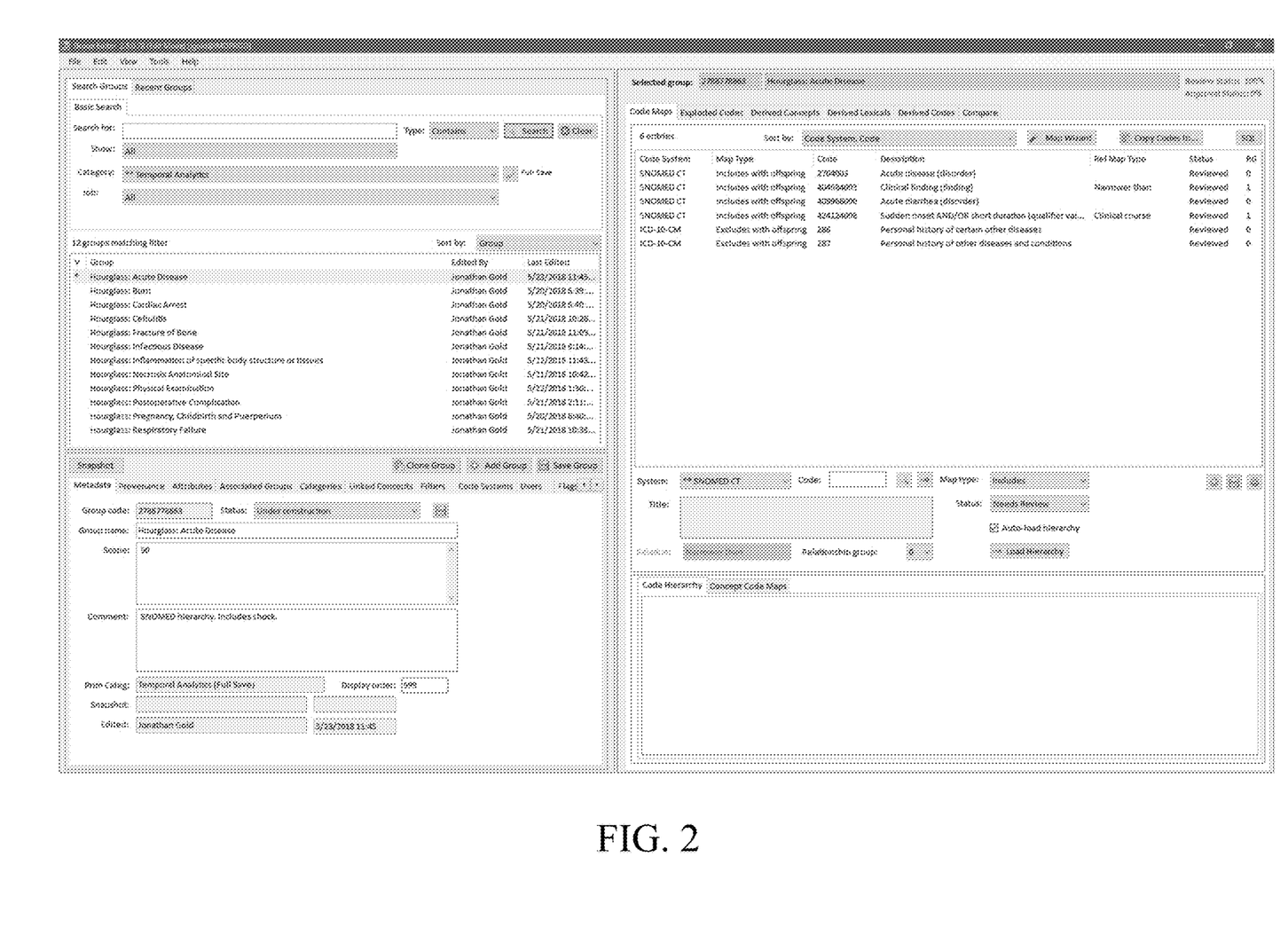
FIG. 2 is a screenshot of an exemplary user interface for generating limited duration problem list groups.
Figure 3:
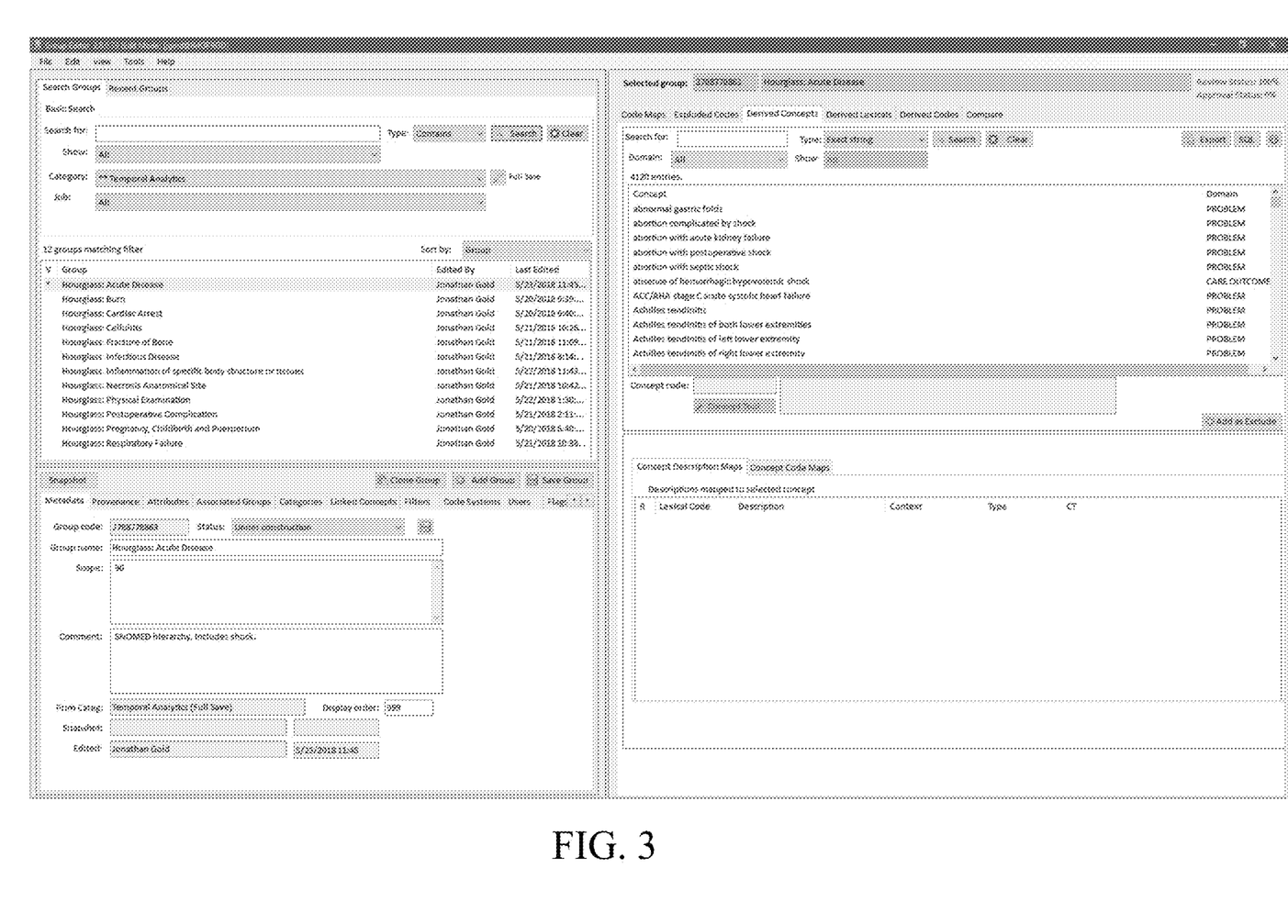
FIG. 3 is a second screenshot of an exemplary user interface for generating limited duration problem list groups.

FIGS. 2 and 3 depict screenshots of a user interface for generating and populating the limited duration groups. In particular, FIG. 2 depicts an interface in which the user may select from among a plurality of existing limited duration groups, such as the "Hourglass: Acute Disease" group shown selected and highlighted in the figure, or create a new limited duration group, e.g., by selecting the "Add Group" option below the listing of existing groups.

Upon selecting an existing group, additional windows in the user interface may be populated with data specific to that group. For example, the system may provide a length of the limited duration window to which the limited duration group belongs, i.e., the DurationDays attribute value for that limited duration group. In one aspect, that value may be read only; in another aspect, the user may be able to use the interface to modify the DurationDays value for the selected group.

In another section of the display, such as the upper-right quadrant of FIG. 2, the system may display each of the external one or plurality of terminologies used to populate the selected limited duration group. For example, FIG. 2 indicates that elements of a first external terminology, i.e., SNOMED CT, are used in an inclusive fashion to build the group and that elements of a second external terminology, i.e., ICD-10-CM, are used in an exclusionary fashion to reduce the number of results returned by the original SNOMED-based build.

Turning to FIG. 3, an additional view of the user interface is depicted in which the "derived concepts" tab is selected in the upper-right quadrant rather than the "code maps" tab of FIG. 2. In this figure, the external terminologies are replaced with an identification of the interface terminology concepts that are derived from, i.e., that map to, the inclusive first external terminology elements depicted in FIG. 2 and that do not also include maps to the exclusionary second external terminology elements of that figure. As discussed above, each of those concepts maps to one or more lexicals, which represent alternative ways to express their respective concepts.

FIG. 2 illustrates that each of the first and second external concepts includes a concept name/description, as well as a unique numeric (or alphanumeric) identifier. While not depicted in FIG. 3, it should be appreciated that the derived interface terminology concepts similarly may include their own unique numeric or alphanumeric identifiers. Additionally, each of the interface terminology lexicals also may include its own unique numeric or alphanumeric identifier.

Figure 4:
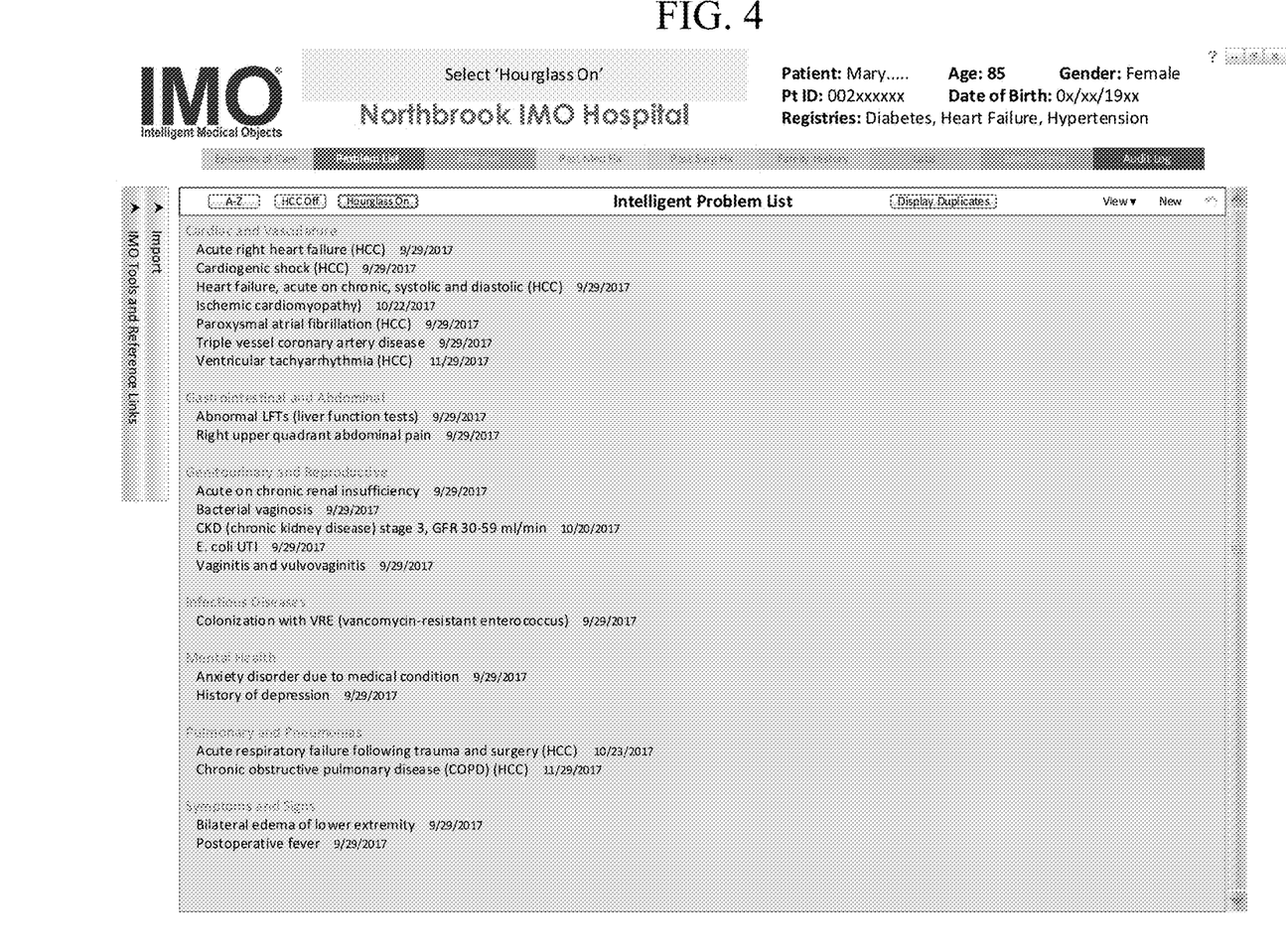
FIG. 4 is a screenshot of an exemplary interactive patient problem list.

Turning now to FIGS. 4-11, exemplary images of the dynamic problem list user interface are presented. In FIGS. 4 and 5, a patient's problem list is presented, with groups of similar problems clustered or categorized together. One manner of generating these clusters may be found in the commonly-assigned U.S. patent publication 2015/0242571, the contents of which are incorporated herein by reference in their entirety. The user interface may permit turning the face sheet optimization feature on and off, e.g., FIG. 4 includes an "Hourglass On" selectable button to turn on the feature, and FIG. 5 replaces that button with an "Hourglass Off" one.

Additionally, once the limited duration feature has been turned on, the system executes the analysis discussed above to identify any problems on the patient's problem list that are categorized within a limited duration window and for which the number of days that have elapsed since the date of entry of the problem is greater than or equal to the DurationDays attribute for that respective limited duration window. That identification may be visually presented to the user by highlighting the text of the relevant problem list entries as compared to the comparatively irrelevant entries. For example, the problems "Acute right heart failure (HCC)," "Cardiogenic shock (HCC)," "Heart failure, acute on chronic, systolic and diastolic (HCC)," "Paroxysmal atrial fibrillation (HCC)," "Acute on chronic renal insufficiency," "Bacterial vaginosis," "*E. coli* UTI," "Vaginitis and vulvovaginitis," "Colonization with VRE (vancomycin-resistant enterococcus)," "Acute respiratory failure following trauma and surgery (HCC)," and "Postoperative fever" are all depicted in FIG. 5 with their text highlighted in a different color as compared to the remaining problem list entries. It will be appreciated that not every problem on or before a certain date has been highlighted as requiring further analysis. For example, while "Acute right heard failure (HCC)" has a problem entry date of Sep. 29, 2017 and is highlighted, several other problems, including "Abnormal LFTs (liver function tests)" and "Anxiety disorder due to medical condition" have the exact same problem entry date and are not highlighted. The reason for this distinction is that the former problem fits within a limited duration group having a limited duration window shorter than the difference between the date of problem entry and the date at which this problem window image is generated, whereas the latter problems either do not fall within a limited duration group or else fall within a group whose limited duration window is longer and has not closed yet.

Figure 6:
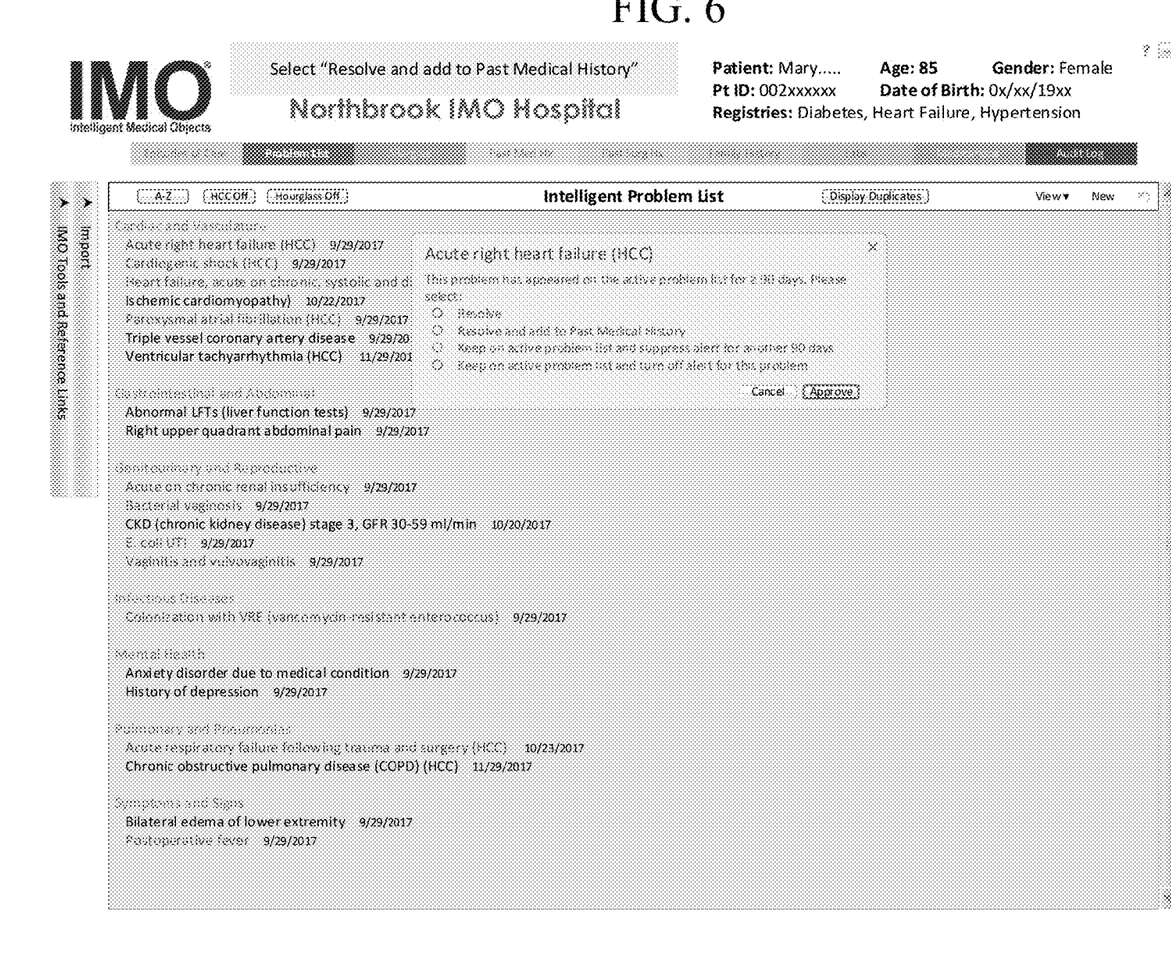
FIG. 6 is a screenshot of the problem list of FIG. 5 after selecting one of the highlighted problems belonging to a limited duration group with a limited duration window that has closed.
Figure 7:
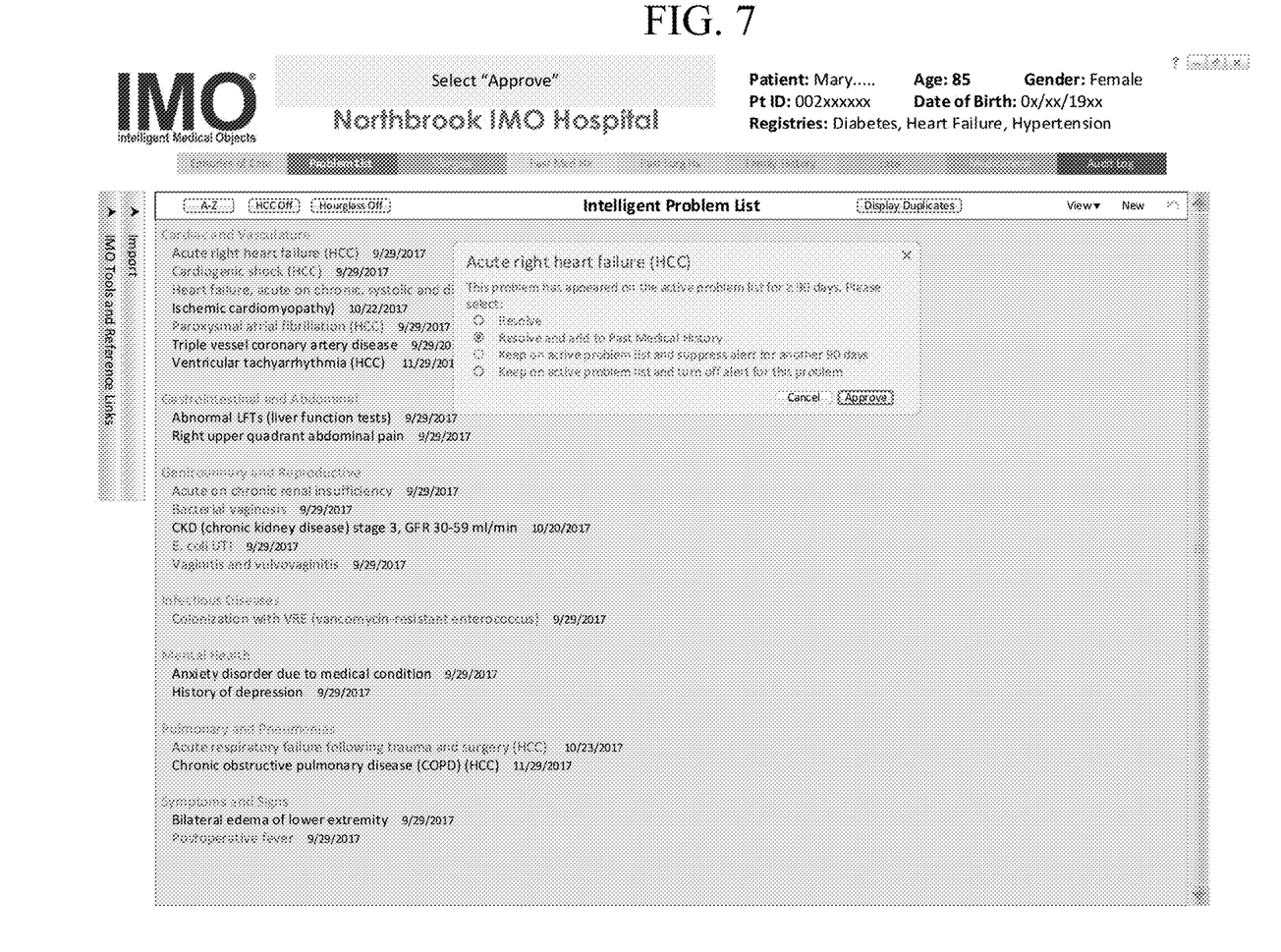
FIG. 7 is a screenshot of the problem list of FIG. 6 indicating a user's selection with regard to how to treat the selected highlighted problem.

In FIG. 6, the user selects the problem "Acute right heart failure (HCC)" and the system generates a pop-up window prompting the user to determine how to handle that problem's representation on the patient's problem list. In this example, the pop-up window includes a plurality of radio buttons prompting the user to determine whether to resolve the problem, i.e., remove it from the problem list altogether, resolve the problem and also add it to the patient's Past Medical History list, keep the problem on the active problem list and suppress the alert for a time period equal to the original duration for the problem's limited duration group, or keep the problem on the active problem list and turn off future alerts. FIG. 7 depicts the user selecting the second of these options, i.e., resolve the problem and add it to the Past Medical History list, and FIG. 8 is an image of the updated problem list with that problem being resolved, i.e., removed from the active problem list.

Figure 9:
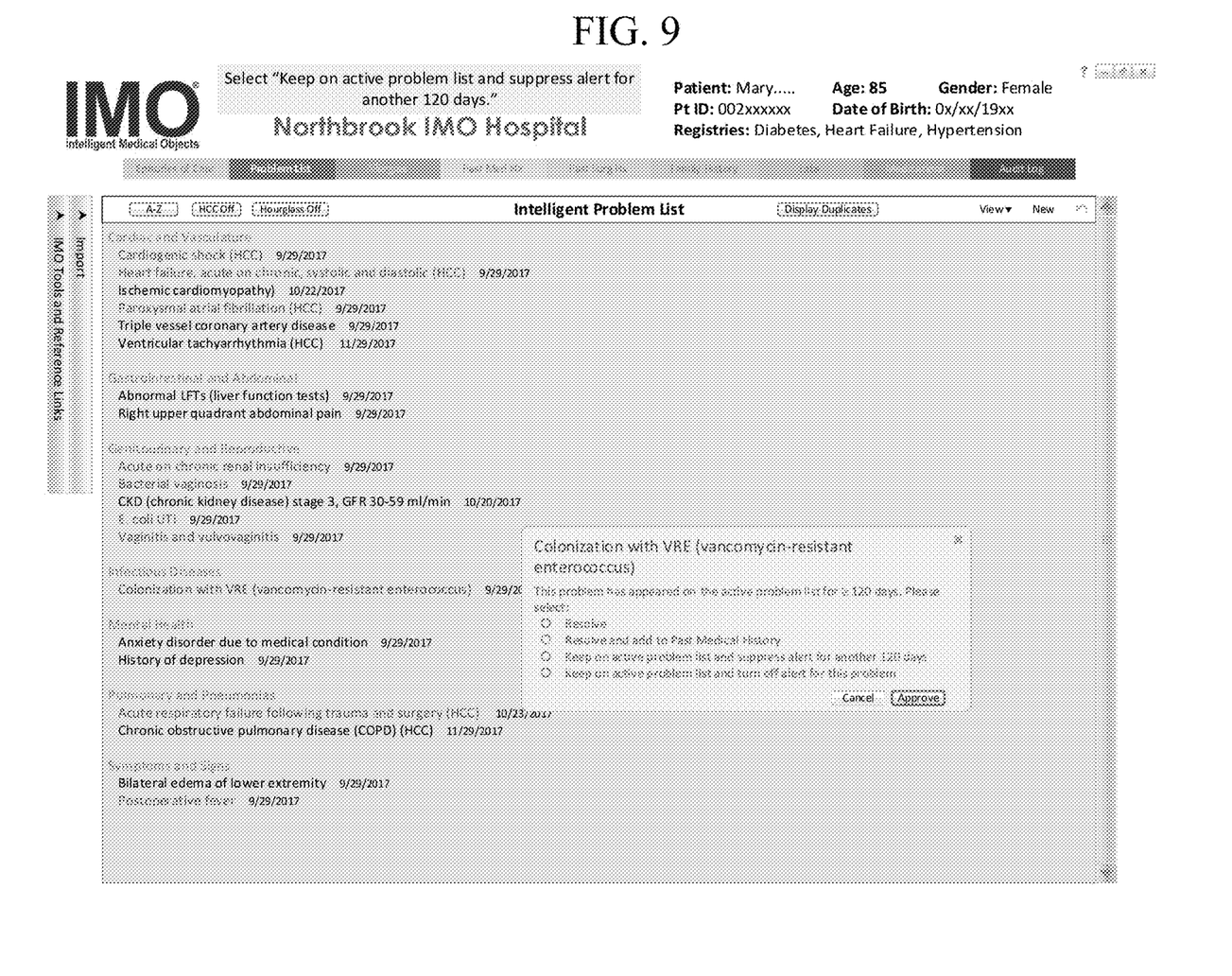
FIG. 9 is a screenshot of the problem list of FIG. 8 after selecting a second one of the highlighted problems as belonging to a limited duration group with a limited duration window that has closed.
Figure 10:
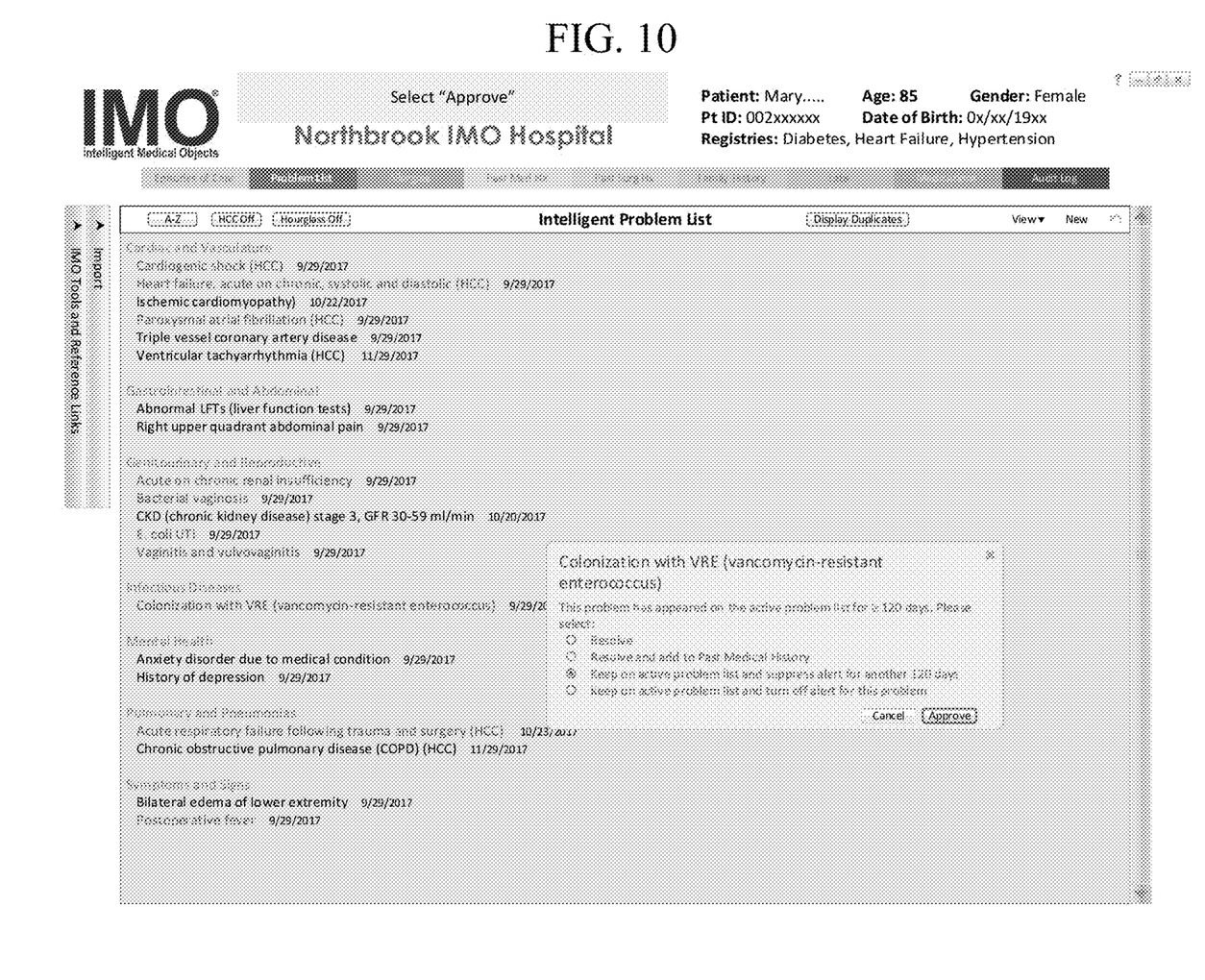
FIG. 10 is a screenshot of the problem list of FIG. 9 indicating a user's selection with regard to how to treat the selected highlighted problem.
Figure 11:
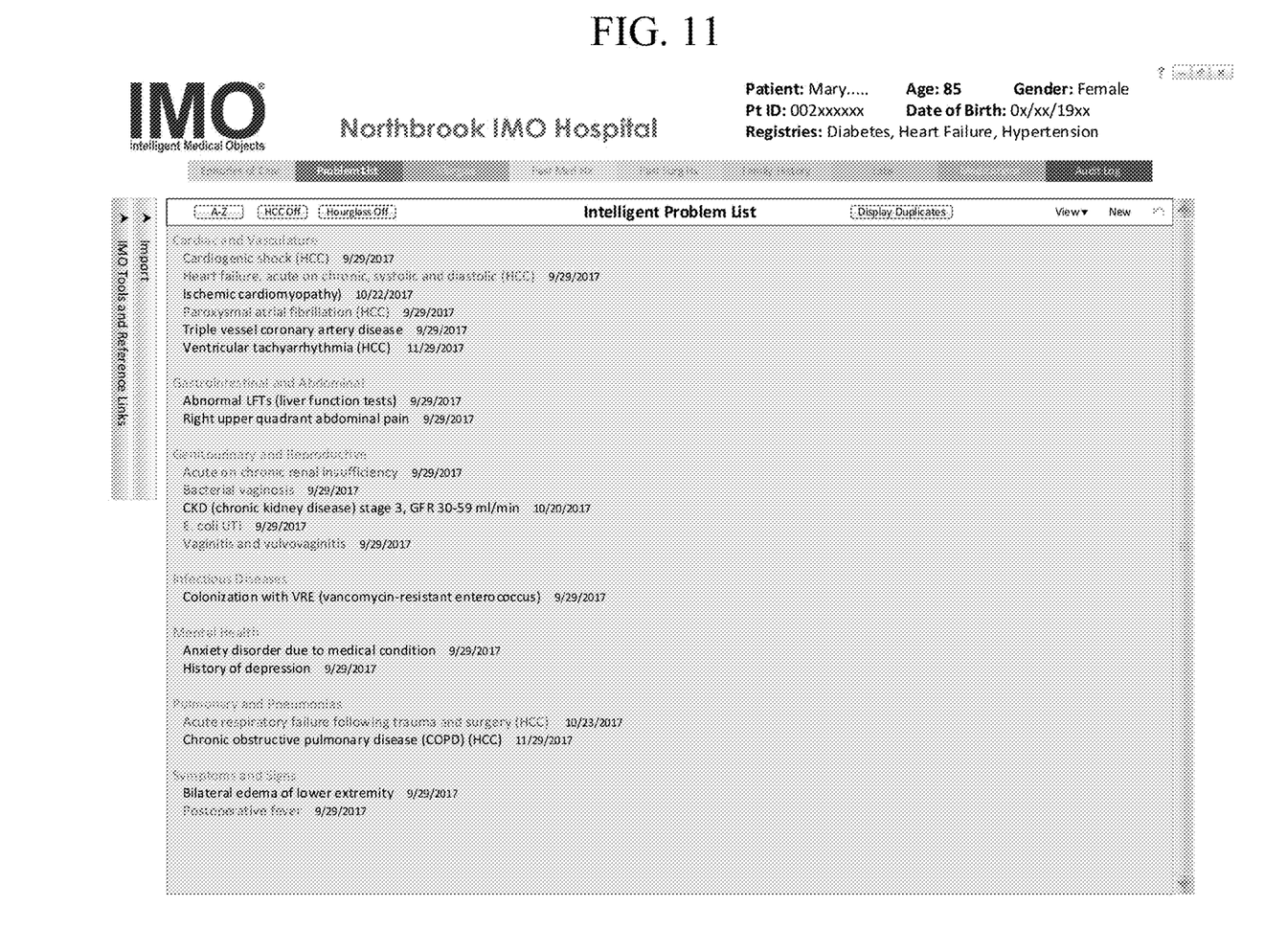
FIG. 11 is a screenshot of the problem list of FIG. 8 after being updated to reflect the user's selection indicated in FIG. 10.

FIG. 9 depicts another interaction between the user and the problem list user interface, this time with the user selecting the highlighted problem "Colonization with VRE (vancomycin-resistant enterococcus)." Whereas the previous problem was outside its 90-day limited duration window, this problem is outside a different, 120-day window. As with the previous example, however, upon selecting the problem, the system generates a pop-up prompting the user to decide how to deal with the problem with respect to its presentation on the patient's problem list. In this case, as seen in FIG. 10, the user decides to keep the problem on the active problem list and suppress an alert for a time period equal to that problem's limited duration group's window, i.e., another 120 days. Upon approving that choice, the system updates the problem list. As seen in FIG. 11, that problem remains on the problem list as per the user's decision, and it goes from a highlighted to un-highlighted state to reflect the decision that it is not currently outside of a limited duration window.

It will be appreciated that this user interface and the underlying methodology used to generate and update that interface permit the user and other subsequent users to quickly view a patient's problem list within an EMR or EHR. By optimizing the display of that list as discussed herein, users are able at a glance to get a better picture of the patient's current condition and to focus on those more timely problems. Additionally, by permitting the problem list to continue to display older problems that a clinician ordinarily would expect to be resolved but for which the patient is experiencing issues or complications, the present user interface, system, and method also may be able to direct the user to those lingering problems that may require additional attention.

As set forth in greater detail herein, the present system and method are operable within a network of computer systems, with a plurality of computers each having a processor configured to operate EMR or EHR software accessible by one or more care providers to document patient encounters. In one aspect, each computer system operates the same EMR or EHR software. In another aspect, the computer systems may operate different EMR or EHR software packages that receive and/or store patient data in different ways. In this latter aspect, however, the various EMR or EHR software packages may interface with a common ontology such as an interface terminology in order to provide a common encoding mechanism for their respective sets of patient data.

While the first and second terminologies are referred to herein as "external," it will be understood that this is to distinguish them from the interface terminology, in that they are separate terminologies and not, e.g., subsets of that terminology. Additionally, it will be appreciated that, while they are referred to as "external," the interface terminology may not be "internal," e.g., with regard to the EMR or EHR software. Instead, the interface terminology may be created and maintained by an entity separate from the EMR or EHR software provider. In this way, the same interface terminology may be used across multiple EMR or EHR software platforms, such that the system may be EMR or EHR-agnostic. Thus, rather than needing to develop a solution for each different EMR or EHR platform, the same system may be usable with each software package, thereby increasing the efficiency of developing and maintaining the system across multiple platforms.

In another aspect, the system may include additional features to clean up a problem list in order to provide a more useful or optimized interface, thereby providing a clinician with faster or easier access to patient problem information. In particular, the system may attempt to remove, consolidate, or reorder problem list entries according to one or more heuristics applied to data underlying those entries.

In one case, the system may remove redundant problem list entries through one or more methods. As discussed above, each problem list entry may be encoded with a lexical of an interface terminology that is mapped to a concept within that terminology. Deduplication may involve removing multiple problem list instances that are mapped to the same interface terminology lexical. Additionally or alternatively, the system may analyze each problem list entry and identify two or more entries that are mapped to different lexicals but, through their respective lexicals, to the same interface terminology concept. Since the lexicals represent semantically different ways to express the same concept, the system may identify the plurality of problems as being conceptually identical and then may prompt the user to select which lexical and its associated semantic meaning to retain on the problem list.

In another instance, the system may identify problems mapped to interface or external terminology concepts that have parent-child or other hierarchical relationships to one another. For example, a patient's problem list may include a first entry mapped to an interface terminology concept for diabetes, a second entry mapped to an interface terminology concept for diabetes with one complication, and a third entry mapped to an interface terminology concept for diabetes with a second complication. In that example, each of the interface terminology concepts may be hierarchically or otherwise related. The system may identify the problems as related, group them together in the interface, and present them to the user with a request for a selection as to one or more problems. Additionally or alternatively, the system may automatically remove or hide from view the broadest/most-parent problem, recognizing that the more specific child concept-mapped problem(s) may convey more relevant information to the user.

In yet another instance, the system may identify one or more problems as being related to a progressive disease, e.g., chronic kidney disease (CKD). Stages for each disease may have their own interface terminology concepts, e.g., stage 1 may map to a different concept than stage 2, which may map to a further different concept than stage 3. The system may be programmed to recognize these different concepts as being related to one another and further to recognize that the presence of a problem mapped to a concept reflecting a later stage should take precedence over a similar problem mapped to a concept reflecting an earlier stage. For example, the system may be programmed to recognize that a patient problem list that includes stage 3 CKD does not also need to include and display stage 2 CKD, such that the system removes or otherwise hides that former problem from the interactive problem list.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

We claim:

1. A system comprising a computer including a processor, the processor configured to generate a dynamically-adjustable user interface for modifying a patient problem list in an electronic medical record or an electronic health record, comprising:
   a first region comprising a patient problem list including a plurality of patient problem list entries, each patient problem list entry including a textual description corresponding to a problem reflected in the patient problem list entry,
   wherein each patient problem list entry is encoded with a date of entry into the patient problem list and each textual description is mapped to at least one concept or lexical of an interface terminology separate from and interfacing with the electronic medical record or electronic health record, the interface terminology structured to include one or more domains including a plurality of concepts within each domain and one or more lexicals linked to each concept,
   wherein the at least one concept or lexical is mapped to at least one external terminology concept,
   wherein the at least one external terminology concept is mapped to at least one limited duration group selected from among a plurality of limited duration groups, each limited duration group comprising a respective grouping of a plurality of external terminology concepts, each limited duration group including a limited duration window,
   wherein a number of days that has elapsed since the date of entry of each patient problem list entry is compared against the limited duration window of the mapped at least one limited duration group, and
   wherein, when the number of days that has elapsed since the date of entry of a patient problem list entry from among the plurality of patient problem list entries is outside the limited duration window of at least one of the mapped at least one limited duration groups, the first region is modifiable to remove the patient problem list entry from the first region.

2. The system of claim 1, wherein the at least one external terminology concept is a Systematized Nomenclature of Medicine concept.

3. The system of claim 1, wherein the at least one concept or lexical is cross-checked against at least one concept of a second external terminology, and wherein the at least one concept or lexical is not mapped to the at least one concept of the second external terminology.

4. The system of claim 3, wherein the second external terminology is ICD-10-CM.

5. The system of claim 1, wherein, when the date of entry of the patient problem list entry is outside the limited duration window of at least one of the mapped at least one limited duration groups, the patient problem list entry is visually distinguished from others of the plurality of patient problem list entries.

6. The system of claim 5, wherein the first region is modifiable to remove the visual distinction and to retain the patient problem list entry in the first region.

7. The system of claim 1, wherein, when the date of entry of the patient problem list entry is outside the limited duration window of at least one of the mapped at least one limited duration groups, the user interface is modifiable to move the patient problem list entry from the first region to a second region.

8. A method for dynamically-adjusting a patient problem list in an electronic medical record or an electronic health record, comprising:
   displaying a patient problem list within an interface associated with the electronic medical record or electronic health record including a plurality of patient problem list entries, each patient problem list entry including a textual description corresponding to a problem reflected in the patient problem list entry,
   encoding each patient problem list entry with a date of entry into the patient problem list and mapping each patient problem list entry textual description to at least one concept or lexical of an interface terminology separate from and interfacing with the electronic medical record or electronic health record, the interface terminology structured to include one or more domains including a plurality of concepts within each domain and one or more lexicals linked to each concept,
   mapping the at least one concept or lexical to at least one external terminology concept,
   mapping the at least one external terminology concept to a limited duration group comprising a respective grouping of a plurality of external terminology concepts, the limited duration group comprising a limited duration window, and comparing a number of days that has elapsed since the date of entry of each patient problem list entry against the limited duration window, wherein, when the number of days that has elapsed since the date of entry of a patient problem list entry from among the plurality of patient problem list entries is outside the limited duration window, the patient problem list is modifiable to remove the patient problem list entry from the patient problem list displayed to a user within the interface associated with the electronic medical record or electronic health record.

9. The method of claim 8, wherein the at least one external terminology concept is a Systematized Nomenclature of Medicine concept.

10. The method of claim 8, wherein the at least one concept or lexical is cross-checked against at least one concept of a second external terminology, and wherein the at least one concept or lexical is not mapped to the at least one concept of the second external terminology.

11. The method of claim 10, wherein the second external terminology is ICD-10-CM.

12. The method of claim 8, wherein, when the date of entry of the patient problem list entry is outside the limited duration window, the patient problem list entry is visually distinguished from others of the plurality of patient problem list entries.

13. The method of claim 12, wherein a first region of the interface is modifiable to remove the visual distinction and to retain the patient problem list entry in the first region.

14. The method of claim 8, wherein, when the date of entry of the patient problem list entry is outside the limited duration window, the interface is modifiable to move the patient problem list entry from a first region to a second region.

* * * * *